(12) United States Patent
Kelnberger et al.

(10) Patent No.: US 10,130,734 B2
(45) Date of Patent: Nov. 20, 2018

(54) ENDOPROSTHETIC COMPONENT

(71) Applicant: CeramTec GmbH, Plochingen (DE)

(72) Inventors: Alfons Kelnberger, Rothenbach (DE);
Heinrich Wecker, Eckental (DE);
Frank Ziermann, Berlin (DE);
Mateusz Juszczyk, Velden (DE)

(73) Assignee: CERAMTEC GMBH, Plochingen (DE)

( * ) Notice: Subject to any disclaimer, the term of this patent is extended or adjusted under 35 U.S.C. 154(b) by 0 days.

(21) Appl. No.: 14/648,009

(22) PCT Filed: Nov. 25, 2013

(86) PCT No.: PCT/EP2013/074576
§ 371 (c)(1),
(2) Date: May 28, 2015

(87) PCT Pub. No.: WO2014/080008
PCT Pub. Date: May 30, 2014

(65) Prior Publication Data
US 2015/0335782 A1    Nov. 26, 2015

(30) Foreign Application Priority Data
Nov. 26, 2012  (DE) .................. 10 2012 221 523

(51) Int. Cl.
*A61K 9/00*  (2006.01)
*A61L 27/10* (2006.01)
(Continued)

(52) U.S. Cl.
CPC .......... *A61L 27/10* (2013.01); *A61F 2/30767* (2013.01); *A61F 2/44* (2013.01); *A61F 2/446* (2013.01); *A61F 2/4455* (2013.01); *A61F 2/4611* (2013.01); *A61L 27/105* (2013.01); *A61L 27/54* (2013.01); *A61L 27/56* (2013.01); *C04B 35/10* (2013.01); *C04B 35/48* (2013.01); *A61F 2002/30004* (2013.01); *A61F 2002/30011* (2013.01); *A61F 2002/30013* (2013.01); *A61F 2002/30014* (2013.01); *A61F 2002/30029* (2013.01); *A61F 2002/3084* (2013.01); *A61F 2002/3092* (2013.01); *A61F 2002/3093* (2013.01); *A61F 2002/30329* (2013.01); *A61F 2310/00023* (2013.01); *A61F 2310/00179* (2013.01); *A61F 2310/00203* (2013.01); *A61F 2310/00239* (2013.01); *A61L 2300/112* (2013.01); *A61L 2430/38* (2013.01);
(Continued)

(58) Field of Classification Search
CPC ...................................................... A61L 27/10
See application file for complete search history.

(56) References Cited

U.S. PATENT DOCUMENTS 6,013,591 A * 1/2000 Ying .................. A61L 27/12
106/35
6,979,353 B2  12/2005 Bresina
(Continued)

FOREIGN PATENT DOCUMENTS

WO    2012/063865 A1    5/2012

*Primary Examiner* — Paul W Dickinson
(74) *Attorney, Agent, or Firm* — Norton Rose Fulbright US LLP

(57) ABSTRACT

An endoprosthetic component which is set up in the implanted state to penetrate in a controlled manner into adjoining bone material.

25 Claims, 2 Drawing Sheets

(51) Int. Cl.
- *A61F 2/44* (2006.01)
- *C04B 35/10* (2006.01)
- *C04B 35/48* (2006.01)
- *A61L 27/54* (2006.01)
- *A61L 27/56* (2006.01)
- *A61F 2/46* (2006.01)
- *A61F 2/30* (2006.01)

(52) U.S. Cl.
CPC ............ *C04B 2235/3217* (2013.01); *C04B 2235/3244* (2013.01); *C04B 2235/3246* (2013.01); *Y10T 428/249969* (2015.04)

(56) References Cited

U.S. PATENT DOCUMENTS

| | | |
|---|---|---|
| 8,211,177 B2 | 7/2012 | Richelsoph |
| 2003/0105527 A1 | 6/2003 | Bresina |
| 2009/0157187 A1 | 6/2009 | Richelsoph |
| 2010/0042216 A1 | 2/2010 | Kilpela et al. |
| 2011/0012280 A1 | 1/2011 | Deslauriers et al. |
| 2011/0111005 A1* | 5/2011 | Zreiqat ............ A61K 6/0612 424/423 |
| 2013/0268078 A1 | 10/2013 | Richelsoph |
| 2013/0274886 A1 | 10/2013 | Matsumoto et al. |

* cited by examiner

ENDOPROSTHETIC COMPONENT

This application is a § 371 of International Application No. PCT/EP2013/074576 filed Nov. 25, 2013, and claims priority from German Patent Application No. 10 2012 221 523.9 filed Nov. 26, 2012.

FIELD OF THE INVENTION

The invention relates to endoprosthetic components. In particular, the invention relates to endoprosthetic components that can be used as spinal implants.

BACKGROUND OF THE INVENTION

Endoprosthetic components, in particular for fusing vertebral bodies, are known. They are adapted in their geometry to the anatomy of the human vertebral body, are located between two vertebral bodies and completely or partially replace the intervertebral disk.

During a first phase of their duration in the human body, they typically keep the vertebral bodies at a distance and in an anatomically correct position solely by means of their mechanical properties. In a second phase, they promote the fusion and thus the growing together of the two surrounding vertebral bodies.

Known components for fusing vertebral bodies are based, for example, on metallic materials such as tantalum or titanium.

Disadvantages of these metallic materials are, for example:
- Metallic abrasion and resulting negative effects on the human organism
- Artifacts in imaging for medical diagnostics
- Effects of aging and long-term performance, such as fatigue, corrosion and the release of metal ions, which can be toxic As a general problem has emerged more and more a risk of infection during surgery, which can be reduced with ceramic components.

Components based on plastics such as highly crosslinked PE (polyethylene) materials or PEEK (polyetheretherketone) are also known.

Disadvantages of plastic components are, for example:
- Insufficient mechanical properties such as the breaking off of prongs or other constituents of the component, for example during installation.
- Lack of presentability in current imaging processes (MRI, X-ray), thereby requiring the use of metallic markers.
- Effects of aging and long-term performance, particularly material fatigue.

Ceramic components based, for example, on silicon nitride, are also known. However, this class of materials was developed with an eye toward excellent high temperature properties—for instance for the machining of metal components for the automotive industry—and for the properties required for this use, such as strength, hardness and long-term stability, ranks rather in the midfield in comparison with other ceramic high-performance materials based on oxidic systems.

In addition, the material is relatively complicated, wherein needle-shaped silicon nitride is embedded in a glass matrix. The sintering of this material is accordingly laborious. The mechanical (post)processing, for example by means of grinding or polishing, is extremely demanding and difficult.

Moreover, components manufactured from silicon nitride have a rather dark coloration—gray to black—which for purely aesthetic reasons encounters a low level of acceptance in the medical field.

All of these disadvantages lead to increased costs in the manufacture of the components, which constitutes a further disadvantage.

A very important aspect of the use of ceramic components for the fusion of vertebral bodies is the generally high stiffness of these materials, which is substantially higher than that of human vertebral bodies.

In certain circumstances, this can cause so-called "stress shielding," which can entail the breakdown of bone material and at least reduces or even eliminates the formation of new bone material. In this case, a fusion of vertebral bodies does not occur.

The principle of this effect can be explained in more detail as follows: Known ceramic cages are generally designed annularly and adapted to the form of the human vertebral body, whereby the ring consists of a monolithic, i.e. dense, solid and highly rigid ceramic. These cages often have a central cavity which is filled either with known bone replacement materials (autologous or allogenic), or have an artificial, porous, osseo-inductive or osseo-conductive structure which is generally considerably less stiff than the outer ring. In this area, the bone cells are to form new bone material, whereby the involved cells require an appropriate mechanical stimulus.

If, now, the forces caused by biomechanical stresses on the component are transmitted through the area with high rigidity, the mechanical stimulus in the central region of the component—that is, where the fusion is to take place—is absent, as the stress is shielded ("stress shielding"). Due to the lack of mechanical stimulus in this area, no bone formation and thus no fusion takes place.

This crucial disadvantage is to be solved by the present invention.

A further significant disadvantage of known solutions is the uncontrolled sinking-in of the components into the bone structure of the vertebral body. This uncontrolled sinking-in may occur if, due to the geometry of the component, a high point load is applied to a relatively soft bone substance.

The bone structure of a vertebral body is varied, for instance, the outer cortical bone substance is significantly denser and more solid than the inner cancellous bone substance. In addition, the bone structure of a human being is dependent on age, and of course also varies between individuals. Depending on the weight and activity level of the person, varying biomechanical stresses act on the vertebral column. As a result, uncontrolled sinking of the components into the vertebral body may occur, which can have diverse complications and consequences.

This disadvantage is to be solved by the present invention.

OBJECTS OF THE INVENTION

Accordingly, the object of the invention is to provide an endoprosthetic component which is particularly suitable for the fusion of vertebral bodies and eliminates or at least reduces the effect of "stress shielding."

The following objects are thereby significant, either individually or in combination:
- The component should have a sufficiently high strength, so that the vertebral bodies are held in a defined position with respect to one another during fusion.

The component should ensure a sufficiently high mechanical stimulation for the formation of new bone material. It is to eliminate "stress shielding" so that the fusion can take place.

The component should ensure a sufficiently high primary stability, i.e. it should remain stable between the vertebral bodies during fusion.

The component should not uncontrollably sink into the bone substance of the vertebral bodies The component should ensure the fusion of two vertebral bodies as quickly and completely as possible.

After fusion, the component should be to a great extent bioinert, i.e. no biological interaction between the component and the surrounding tissue should occur. In particular, no harmful wear particles should be formed, which are distributed throughout the vascular system in the human body and can entail uncontrollable reactions.

BRIEF DESCRIPTION OF THE INVENTION

The object is achieved with an endoprosthetic component having the features of the present invention. Advantageous embodiments of this article are described herein.

DETAILED DESCRIPTION

Figure 1:
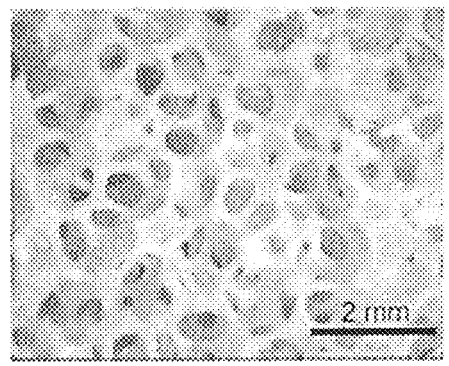
FIG. 1 shows one possible implementation of ceramic material according to the present invention.

An endoprosthetic component according to the invention comprises a first region and a second region, wherein the material of the first region has a greater strength than the material of the second region. The first region is constructed so as to penetrate in a controlled manner into adjacent bone material in the implanted state.

Especially preferably, the endoprosthetic component is a vertebral column implant, in particular a cage. In other words, the use of such an endoprosthetic component as a vertebral column implant, in particular as a cage, is preferred.

In the context of this invention, controlled penetration is understood to mean that only component parts provided for the penetration of the bones/vertebrae penetrate into the bones/vertebrae to a predetermined maximum depth. An uncontrolled sinking-in of component parts not provided for penetration into the bones/vertebrae is not to be included within this concept.

This can be advantageously achieved in that at least one part of a surface of the first region protrudes over a surface of the second region. The part of the first region protruding over the surface of the second region can then be designed such that it can penetrate into the adjacent vertebral bodies in a controlled manner. One possible embodiment could consist of spikes or pins that protrude over the surface of the second region and in an implanted state bore into the surface of the adjacent vertebral body. By means of the length and the diameter of the pins, a maximum penetration depth can be defined such that the penetration is controlled.

According to a preferred embodiment of the invention, the first outer region of the component partially or completely encloses the second inner region.

The first region is preferably composed of densely sintered, monolithic ceramic.

This means that the first region is substantially non-porous, i.e. preferably of a porosity of less than 5 vol.-%, more preferably of a porosity of less than 3 vol.-% and especially preferably of a porosity of less than 1 vol.-%.

The materials to be employed are preferably oxidic material classes such as the class of aluminum or zirconium oxides or any mixtures thereof.

According to the invention, aluminum oxides also include zirconium oxide-reinforced materials, for example ZTA-materials (zirconia toughened [sic] alumina); Zirconium oxides cover all types of tetragonal stabilized or partially stabilized zirconium oxides such as yttrium, cerium or gadolinium-stabilized zirconium oxides. Also conceivable are zirconium oxide-based composite materials with aluminum oxide-containing fractions for reinforcement, so-called ATZ materials.

Since these materials have high strengths, it is ensured that the component as a whole has a sufficiently high strength. The standard measured 4-point bending strengths of these materials are in the range between around 500 to almost 2000 MPa.

The second inner region comprises a porous ceramic, which in principal may, but need not, be the same material as or a similar material to the first region. According to a preferred embodiment, the material of the inner first and/or the outer second region can be bioactivated by means of further additions of bioactive substances. Here are possible, for example, layers, regions, admixtures of known bioactive substances in the material from which the first and/or second region are manufactured, or also coatings of at least parts of the surfaces of these regions. However, the bioactive substances can also be disposed in the pores of the second region.

Particularly suitable are substances based on calcium phosphate, such as hydroxyapatite (HA) or tricalcium phosphate (TCP), any forms of modified HA coatings, in which the Ca-atoms are replaced by elements of the alkali metal or alkaline earth metal group such as Na, K, or Mg, Sr, but also for example Si.

Particularly suitable are also glass-like substances such as bioglasses. Preferably used is a bioglass which comprises as main components $SiO_2$ (silicon dioxide), CaO (calcium oxide), $Na_2O$ (sodium superoxide) and $P_2O_5$ (phosphorus pentoxide).

For biofunctionalization in terms of promoting and stimulating bone growth, all types of coatings which serve a biomimetic approach and so provide the cells involved in bone formation optimal conditions for osteogenesis can also be used. These can be nanostructured HA coatings or covalently bonded phosphating layers.

Clearly evident to one skilled in the art, the first and/or second region of the endoprosthetic component can of course be manufactured from other ceramics than those enumerated, in particular from silicon nitride or any other materials, for example from plastics such as PE, PEEK or tissue-compatible metals such as titanium, as long as these materials fulfill the stated requirements.

The internal structure of the second inner region has a crucial influence on the osseoconductivity of the component, and thus on the capacity to form new bone material. Porous, trabecular structures are particularly suited for the stimulation of new bone formation. These structures are very similar to the structure of cancellous bone and provide optimal conditions for the growth of the cells involved in bone formation.

The following parameters are thereby critical:
Pore sizes between 100 and 1000 µm, preferably between 400 and 600 µm
Porosities between 75 and 85 vol.-%
Interconnectivity, i.e. the individual pores are interconnected and allow optimal vascularization of the component FIG. 1 shows one possible implementation of these requirements in ceramic material. Here, an interconnective porosity with the preferred pore size of 400 to 600 µm is realized in a ZTA-ceramic.

The mechanical properties of the second interior region are highly dependent on the material composition and on the structure. However, this also means that the mechanical characteristics of the inner region can be selectively set and adjusted to the biological environment into which they are to be introduced by means of the selection of the material and the design of the structure. As a rule, the second, trabecular region of the component is less firm and less stiff than the first, outer region of the component. Also conceivable, however, are structures in which the first stiff region is provided on the inside of the component, for example as a pillar, and the second trabecular region is disposed around this pillar.

In principle, the actual disposition of these two regions is unlimited. The only essential requirements are the presence of the two regions and the fulfillment of the objects in the component.

Compressive strengths of such trabecular ceramic structures are typically in the range of 5 to 10 MPa. However, through the use of suitable production methods, compressive strengths in the upper double-digit megapascal region can also be achieved. Depending on the geometry, the respective stiffnesses are in the range of 5 to 50 GPa.

Crucial for the component according to the invention are the combination of these two regions and the design of the component resulting from the combination.

If the first outer region is too solid, the already described effect of "stress shielding" results due to the high rigidity of the monolithic ceramic material. The component as a whole thus loses its fusion function. The second, inner area is shielded from stress, and no bone formation occurs due to the lack of mechanical stimulation.

However, a solid outer region allows a large contact surface of the mechanically strong first region of the component against the vertebral bodies, thereby counteracting the sinking-in of the component.

If one minimizes the structural rigidity in order to avoid "stress shielding" through reduction of the first outer region relative to the second inner region, and if this is then realized too weakly, for instance through a too thin wall thickness, the component can thus sink uncontrolled into the adjacent vertebral body.

A low wall thickness of the first outer region can also lead to a too low overall level of mechanical stability of the component, so that a risk of fracture of the component, especially during the fusion phase, exists.

According to a particularly preferred embodiment of the invention, the bearing surface of the first region is reduced such that the strength of the component is still sufficiently high to ensure the mechanical stability of the component as a whole. As a result, the overall structural rigidity of the component diminishes and approaches that of a vertebral body. This reduces the risk of "stress shielding."

Typical wall thicknesses for the first region lie in the range of a few millimeters, depending on whether the component is for the lumbar or cervical region. Typical values for cervical components are between 2 and 3 mm, for lumbar components 4 and 6 mm.

To avoid the uncontrolled sinking-in ("subsidence") of the implant into the vertebral body, the first region has on its bearing surfaces structures, for example a peripheral spike or prongs, that enable and facilitate a defined penetration of the component into the vertebral bodies.

Ideally, the structures of the first region penetrate the vertebral body to the point where the porous second region lies flat against the two adjacent vertebral bodies.

This ideal case can be exacted both as part of the surgery as well as promoted by further structural details of the component.

A preferred embodiment of the invention thus provides that the first region is designed in such a way as to penetrate so deeply into the adjacent bone material that at least a portion of the surface of the second region is in contact with the bone material, so that a force transmission between the bone material and the surface of the second region occurs. This embodiment has precisely the advantage that, due to the design, a force shielding of the second region cannot occur, and therefore optimal conditions for the stimulation of bone formation in this area are created.

Figure 2A:
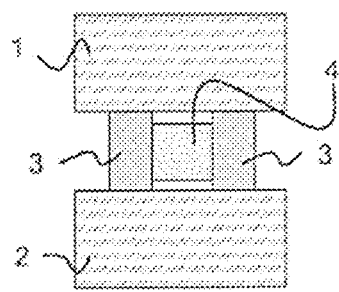
FIG. 2a shows a conventional vertebral column cage, which is disposed between two vertebrae 1 and 2.

A schematic example of such an embodiment is shown in FIG. 2. FIG. 2a shows a conventional vertebral column cage, which is disposed between two vertebrae 1 and 2. The first outer region 3 has an annular shape and surrounds the second inner region 4. The inner region 4 has a smaller height than the outer ring 3 and thus is not in contact with the surfaces of the adjacent vertebrae. Such a design results in the described "stress shielding." In addition, there exists the danger of an uncontrolled sinking-in of the component into the surfaces of the adjacent vertebral bodies.

Figure 2B:
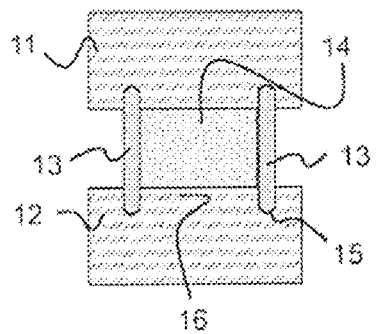
FIG. 2b shows an embodiment of the invention.

FIG. 2b shows a possible embodiment of the invention. Here, too, the first outer region comprises a monolithic ceramic ring 13 which encloses a porous ceramic filling, the second inner region 14. However, unlike the conventional component of FIG. 2a, the ceramic ring 13 is realized significantly less strongly, and protrudes over the second inner region 14 above and below. The upper and lower edge 15 of the ceramic ring 13 is pointedly-shaped, so that these regions can easily penetrate into the surfaces 16 of the adjacent vertebral bodies 11 and 12. Of course, other elements which allow penetration are also possible, such as isolated spikes. It is essential that the penetration occurs in a controlled manner. In the embodiment shown in FIG. 2b, this is ensured firstly in that only the parts which are provided for penetration can also penetrate. Secondly, the maximum depth of penetration is limited by the porous filling of the inner second region. By means of this design, it is thereby simultaneously ensured that the second inner region comes in contact with the surfaces of the adjacent vertebral bodies, and exerts a mechanical stimulation thereon. The dangers of "stress shielding" and uncontrolled sinking into adjacent vertebral bones are thereby effectively minimized.

A further preferred feature relates to the connection of the first region to the second region.

Figure 3A:
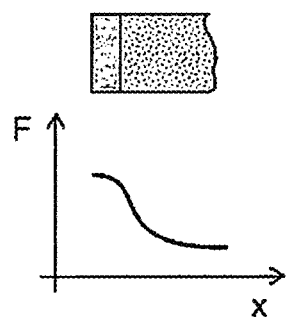
FIG. 3a shows the force curve in the cross section of a cage with a fixed connection between the first and the second region; the curve is continuous.
Figure 3B:
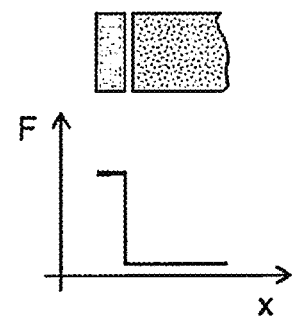
FIG. 3b shows the force curve in the cross section of a cage with a movable connection.

A different load distribution results depending on whether the two regions are fixedly or movably interconnected. In the first case, a continuous load transfer results between the two regions, in the second case discontinuous. FIG. 3a shows the force curve in the cross section of a cage with a fixed connection between the first and the second region. The curve is continuous. FIG. 3b shows the force curve in the cross section of a cage with a movable connection. The curve is discontinuous.

A discontinuous load transfer is more favorable for fusion, as the different rigidities can be adjusted in an uncoupled manner. In particular, the trabecular second region can be ideally adjusted to the stiffness of the vertebral body, due to its structure and material composition. The micromechanical movements and thereby the mechanical stimulus for the formation of new bone can thus be adjusted optimally and independently from the first region, which provides for mechanical stability and primary stability.

Therefore, a particularly preferred embodiment provides that the first region is movably connected to the second region.

The details of the configuration of the movable connection are open. It is crucial that the trabecular second region lies flat against the adjacent vertebral bodies after implantation, and that the first monolithic region can penetrate evenly and in a defined manner into the vertebral bodies.

Figure 4:
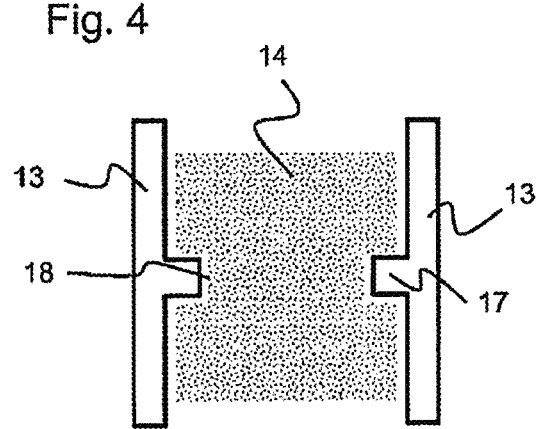
FIG. 4 shows an embodiment of the invention in which the annular or square outer first region is movably connected with the inner second region.

FIG. 4 shows a possible embodiment in which the annular or square outer first region 13 is movably connected with the inner second region 14. By means of a circumferential strip 17 on the inner wall of the outer first region 13 and a matching recess 18 in the side wall of the inner second region, the porous filling of the second recess is movably held in the monolithic ring of the first region 13.

It is claimed:

1. An endoprosthetic component comprising:
   a first outer region; and
   a second inner region;
   wherein the material of the first outer region has a greater 4-point bending strength than the material of the second inner region,
   wherein the second inner region has pores with pore sizes between 100 and 1000 μm; and
   wherein top and bottom surfaces of the first outer region extend beyond respective end surfaces of the second inner region.

2. The endoprosthetic component according to claim 1, wherein the first outer region is designed in such a way as to penetrate so deeply into the adjacent bone material that at least a portion of the surface of the second inner region is in contact with the bone material so that a force transmission between the bone material and the surface of the second inner region occurs.

3. The endoprosthetic component according to claim 1, wherein the first outer region is movably connected to the second region.

4. The endoprosthetic component according to claim 1, wherein the first outer region is substantially non-porous.

5. The endoprosthetic component according to claim 1, wherein the second inner region is porous, wherein the porosity preferably lies between 75 and 85 vol.-%.

6. The endoprosthetic component according to claim 1, wherein the second inner region has pores with a pore size of 1000 μm.

7. The endoprosthetic component according to claim 1, wherein the second inner region has pores with a pore size of 100 μm.

8. The endoprosthetic component according to claim 1, wherein both the first outer region and the second inner region comprises a ceramic.

9. The endoprosthetic component according to claim 1, wherein the at least one of the first outer region and the second inner region further comprises a bioactive substance.

10. The endoprosthetic component according to claim 9, wherein the bioactive substances are admixed with material from which at least one of the first outer region and the second inner region is manufactured, or wherein the bioactive substance is contained in the material in layers or sections.

11. The endoprosthetic component according to claim 9, wherein at least one of the first outer region and the second inner region is coated at least in at least a section thereof with the bioactive substance.

12. The endoprosthetic component according to claim 9, wherein the bioactive substances are disposed in the pores of the second inner region.

13. The endoprosthetic component according to claim 9, wherein the bioactive substance comprises at least one member selected from the group consisting of hydroxyapatite, tricalcium phosphate and bioglass.

14. The endoprosthetic component according to claim 1, wherein the component is a vertebral column implant.

15. The endoprosthetic component according to claim 4, wherein the first outer region has a porosity of less than 5 vol.-%.

16. The endoprosthetic component according to claim 1, wherein the second inner region has pores with pore sizes between 400 and 600 μm.

17. The endoprosthetic component according to claim 1, wherein the oxide ceramic is zirconium oxide.

18. The endoprosthetic component according to claim 1, wherein the oxide ceramic comprises aluminum oxide.

19. The endoprosthetic component according to claim 1, wherein the oxide ceramic comprises at least one member selected from the group consisting of aluminum oxide and zirconium oxide.

20. The endoprosthetic component according to claim 1, wherein at least one of the first outer region and the second region comprises zirconium oxide.

21. The endoprosthetic component according to claim 1, wherein at least one of the first outer region and the second inner region comprises a ceramic selected from the group consisting of a ZTA ceramic, a tetragonally stabilized zirconium oxide, a partially stabilized zirconium oxide and a ZTA ceramic.

22. The endoprosthetic component according to claim 1, wherein at least one of the first outer region and the second inner region comprises a ceramic selected from the group consisting of an yttrium stabilized zirconium oxide, a cerium stabilized zirconium oxide and a gadolinium-stabilized zirconium oxide.

23. The endoprosthetic component according to claim 9, wherein the bioactive substance comprises a bioglass.

24. The endoprosthetic component according to claim 23, wherein the bioglass comprises at least one member selected from the group consisting of $SiO_2$, $CaO$, $Na_2O$ and $P_2O_5$.

25. The endoprosthetic component according to claim 23, wherein the point bending strength is 500-2000 Mpa.

* * * * *